United States Patent
Finnestad et al.

(10) Patent No.: US 8,584,885 B2
(45) Date of Patent: Nov. 19, 2013

(54) MAILBOX STYLE SHARPS CONTAINER

(75) Inventors: Mark Brian Finnestad, Franklin, MA (US); Piyush J. Reshamwala, Hazlet, NJ (US); Robert A. Brown, Algonquin, IL (US)

(73) Assignee: Covidien LP, Mansfield, MA (US)

( * ) Notice: Subject to any disclaimer, the term of this patent is extended or adjusted under 35 U.S.C. 154(b) by 827 days.

(21) Appl. No.: 12/304,352

(22) PCT Filed: Jul. 5, 2007

(86) PCT No.: PCT/US2007/015581
§ 371 (c)(1),
(2), (4) Date: Sep. 29, 2009

(87) PCT Pub. No.: WO2008/005537
PCT Pub. Date: Jan. 10, 2008

(65) Prior Publication Data
US 2010/0155400 A1  Jun. 24, 2010

Related U.S. Application Data

(60) Provisional application No. 60/819,045, filed on Jul. 7, 2006.

(51) Int. Cl.
*B65D 51/18* (2006.01)
*B29C 33/00* (2006.01)
*C08L 83/00* (2006.01)

(52) U.S. Cl.
USPC .................. 220/254.3; 264/240; 524/506

(58) Field of Classification Search
USPC ................. 220/200, 254.3; 264/240; 524/506
See application file for complete search history.

(56) References Cited

U.S. PATENT DOCUMENTS

| | | | | |
|---|---|---|---|---|
| 2,719,123 A * | 9/1955 | Merker et al. | | 508/203 |
| 4,291,084 A * | 9/1981 | Segal | | 428/212 |
| 6,022,924 A | 2/2000 | Akao et al. | | |
| 6,348,540 B1 * | 2/2002 | Sugioka et al. | | 524/577 |
| 6,828,010 B2 * | 12/2004 | Kubota et al. | | 428/213 |
| 6,919,129 B2 * | 7/2005 | Longmoore | | 428/343 |
| 2003/0213714 A1 | 11/2003 | Moats | | |
| 2007/0237916 A1 * | 10/2007 | Rasmussen et al. | | 428/35.2 |
| 2008/0090961 A1 * | 4/2008 | Li et al. | | 525/63 |

OTHER PUBLICATIONS

International Search Report dated Jan. 2, 2008, application No. PCT/US2007/015581.

* cited by examiner

*Primary Examiner* — J. Gregory Pickett
*Assistant Examiner* — James Way
(74) *Attorney, Agent, or Firm* — Lisa E. Winsor, Esq.

(57) ABSTRACT

A closure (26) for a medical waste receptacle through which medical waste is deposited is provided. The closure comprises a door (20) forming at least a portion of the passage, wherein the door is formed from a molded thermoplastic material comprising a polyolefin resin, a nucleating agent and a siloxane processing aid.

14 Claims, 3 Drawing Sheets

US 8,584,885 B2

MAILBOX STYLE SHARPS CONTAINER

CROSS REFERENCE TO RELATED APPLICATIONS

This application claims the benefit of the filing date of the provisional application entitled "MAILBOX STYLE SHARPS CONTAINER" filed Jul. 7, 2006 and assigned Ser. No. 60/819,045, the contents of which are incorporated herein by reference.

FIELD OF THE INVENTION

This invention relates to a molded door of a closure for a medical waste receptacle. More specifically, this invention relates to a molded door including a nucleating agent and an internal release agent.

BACKGROUND OF THE INVENTION

In hospitals, clinics, and similar medical institutions, contamination continues to be of utmost concern. The prevention of the spread of communicable diseases is a major priority; therefore, disposable, single-use, patient care products have become prevalent. Such items are contaminated, once used, and can readily transmit disease. These items include such devices as hypodermic needles, intravenous needles, razors, scalpel blades, or other sharps—all of which are required to be disposed of at their point of usage under current guidelines of the United States Centers for Disease Control.

Various disposal containers for medical wastes have been proposed for the purpose of preventing an individual from gaining access to contaminated items such as sharps once the wastes have been deposited into the container, and many such disposal containers go far to accomplish this purpose. One such container is illustrated in U.S. Patent Application No. 2003/0213714 to Moats et al., which is incorporated herein by reference in its entirety.

Referring to FIGS. 1-3 of Moats et al., reproduced herein as FIGS. 1-3, a counter-balanced door 20 is initially biased to an open position, as illustrated in FIG. 1. When a soiled sharp is placed on the support surface 24 of the door 20, it slides or rolls down the support surface 24 causing the door 20 to rotate under the weight of the sharp. The door 20 rotates backwards about its pivot axis 22 toward the closed position illustrated in FIG. 3, and the sharp slides off of the surface of the door 20 and descends into the medical waste receptacle 12. The contoured portion 28 (commonly referred to as a cowl) of the lid 26 deflects the sharp toward the medical waste receptacle 12.

The disposal of small sized sharps presents a significant challenge, as a small sharp may not have adequate mass or inertia to slide down the surface of a door, in some circumstances. In such case, the medical professional must manually rotate the door in order to dispose of the soiled sharp. However, this manual action contradicts the purpose of the counter-balanced door, which is to limit any direct contact between the medical professional and the medical waste disposal system.

In view of the foregoing challenge, it would be beneficial to minimize the coefficient of friction between the door and the medical waste. Decreasing the coefficient of friction would promote sliding or rolling of the small sized sharps along the surface of the door and preclude the medical professional from physically contacting the medical waste disposal system. Accordingly, it is desirable to enhance the material properties of the pivoting door to minimize the coefficient of friction between the pivoting door and the medical waste positioned thereon.

Furthermore, a door of a medical waste disposal system is commonly formed from a polymeric material using an injection molding or other molding process. A conventional molded part may exhibit warpage and/or exhibit poor dimensional stability. If a counterbalanced door, such as the door 20 illustrated in Moats et al., is dimensionally unstable or significantly warped, it may not rotate properly. A dimensional instability and/or warpage shifts the center of gravity of the door, thereby inhibiting or disturbing the auto-rotation feature. Moreover, a dimensional instability may undesirably cause the door to inadvertently contact another surface of the disposal system, yet again inhibiting or disturbing the auto-rotation feature of the door. Accordingly, it is also desirable to enhance the material properties of the counterbalanced door to minimize any dimensional instability or warpage.

SUMMARY OF THE INVENTION

According to one aspect of the invention, a closure for a medical waste receptacle through which medical waste is deposited is provided. The closure comprises a door forming at least a portion of the passage, wherein the door is formed from a molded thermoplastic material comprising a polyolefin resin, a nucleating agent and a siloxane processing aid.

According to another aspect of the invention, a molded thermoplastic material is provided. The molded thermoplastic material comprises a polyolefin resin, a siloxane processing aid and a nucleating agent.

According to yet another aspect of the invention, a closure for a medical waste receptacle providing a passage through which medical waste is deposited is provided. The closure comprises a door forming at least a portion of said passage, wherein the door is formed from a molded material comprising a polyolefin resin, a siloxane processing aid and a nucleating agent.

According to still another aspect of the invention, a method of forming an article embodying at least a portion of a passage through which medical waste is deposited is provided. The method comprises the steps of preparing a resin comprising a polyolefin resin, a nucleating agent and a siloxane processing aid, and distributing the resin into a mold cavity.

BRIEF DESCRIPTION OF THE DRAWINGS

The invention will be described with reference to the exemplary embodiments illustrated in the figures of which.

DETAILED DESCRIPTION OF THE INVENTION

Figure 1:
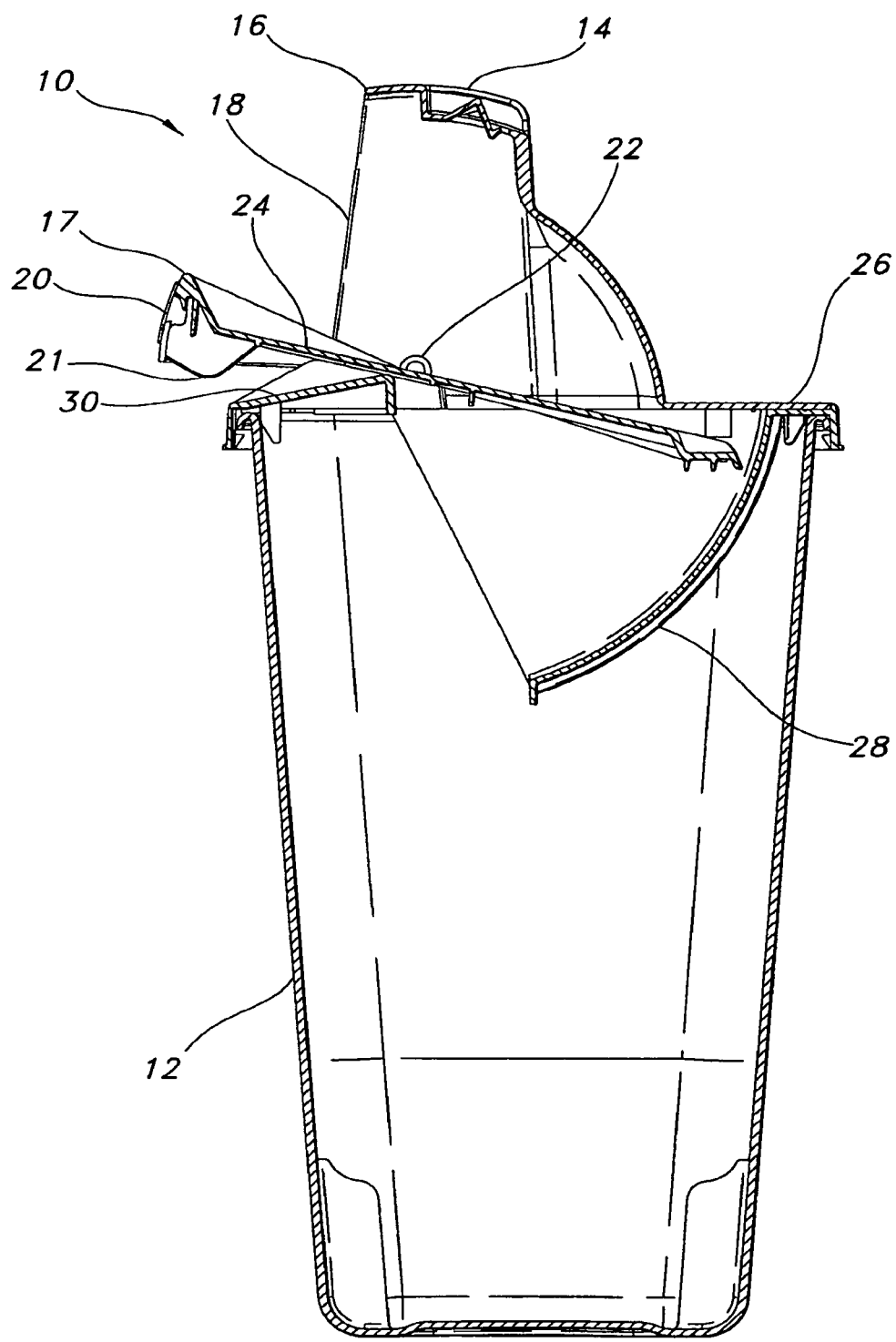
FIG. 1 is a right side cross-sectional view of an embodiment of an assembly having a closure (in its opened position) according to aspects of this invention.

Although the invention is illustrated and described herein with reference to specific embodiments, the invention is not intended to be limited to the details shown. Rather, various modifications may be made in the details within the scope and range of equivalents of the claims and without departing from the invention.

The pivoting door of a medical waste disposal system is commonly formed from a polymeric material by an injection molding process. Briefly, in the injection molding process, a polymeric material, which is commonly called resin, is heated and fed into a mold cavity. The resin conforms to the particular shape of the mold cavity, and is permitted to cool and solidify. Thereafter the formed article is ejected from the mold.

In order to achieve rapid cycle time, the molded article must eject from the mold cavity rapidly, while maintaining dimensional stability and uniformity. To facilitate the rapid release of the article from the mold cavity, externally applied release agents have been conventionally applied to the mold cavity surfaces. However, as is well known, utilizing externally applied release agents yields numerous undesirable consequences such as, for example, non-uniform application of the release agent, build-up of the external release agent on surfaces of the mold, and contamination of the surface of the molded article. These consequences degrade the smoothness, sheen and gloss characteristics of the article surface. The surfaces of such molded articles commonly have a matte appearance due to the external release agents applied to the mold surfaces. Moreover, the externally applied release agents must be applied to the mold cavity after each cycle, which increases cycle time.

For these reasons, molded polymer parts used in accordance with the invention include siloxane processing aids in the form of ultrahigh molecular weight polymers ($M_w$>15,000,000 cSt) dispersed in a thermoplastic resin. By way of non-limiting example, the thermoplastic resin may be, for example, a polyolefin such as polypropylene and polyethylene. In the molding process, the siloxane polymers migrate to and modify the exterior surfaces of the molded polyolefin part. The siloxane processing aids form a uniform dispersion within the thermoplastic polyolefin (TPO) melt, improving melt flow during processing and the lubricity of the processed part. The siloxane processing aids result in molded polyolefin parts having reduced coefficients of friction and improved slip, thereby easing ejection and release of the molded polyolefin part from the mold tooling.

In addition to the aforementioned processing advantages, it has been discovered that modifying polyolefin parts using siloxane processing aids are particularly beneficial for a counterbalanced door of a medical waste disposal system. The resulting molded polyolefin part exhibits decreased surface energy, decreased warping and fatigue during reported use, and improved abrasion resistance. It follows that the coefficient of friction of the external surfaces of the door is also decreased.

As discussed in the Background section, it is advantageous to minimize the coefficient of friction between a pivoting door of a medical waste disposal system and the medical waste being disposed of. The resulting decreased coefficient of friction of the polyolefin door promotes sliding or rolling of small sized sharps along the surface of the door and precludes the medical professional from physically contacting the medical waste disposal system. Moreover, the improved abrasion resistance is especially useful in disposal systems including siloxane in view of the repeated disposal of sharp objects.

Figure 3:
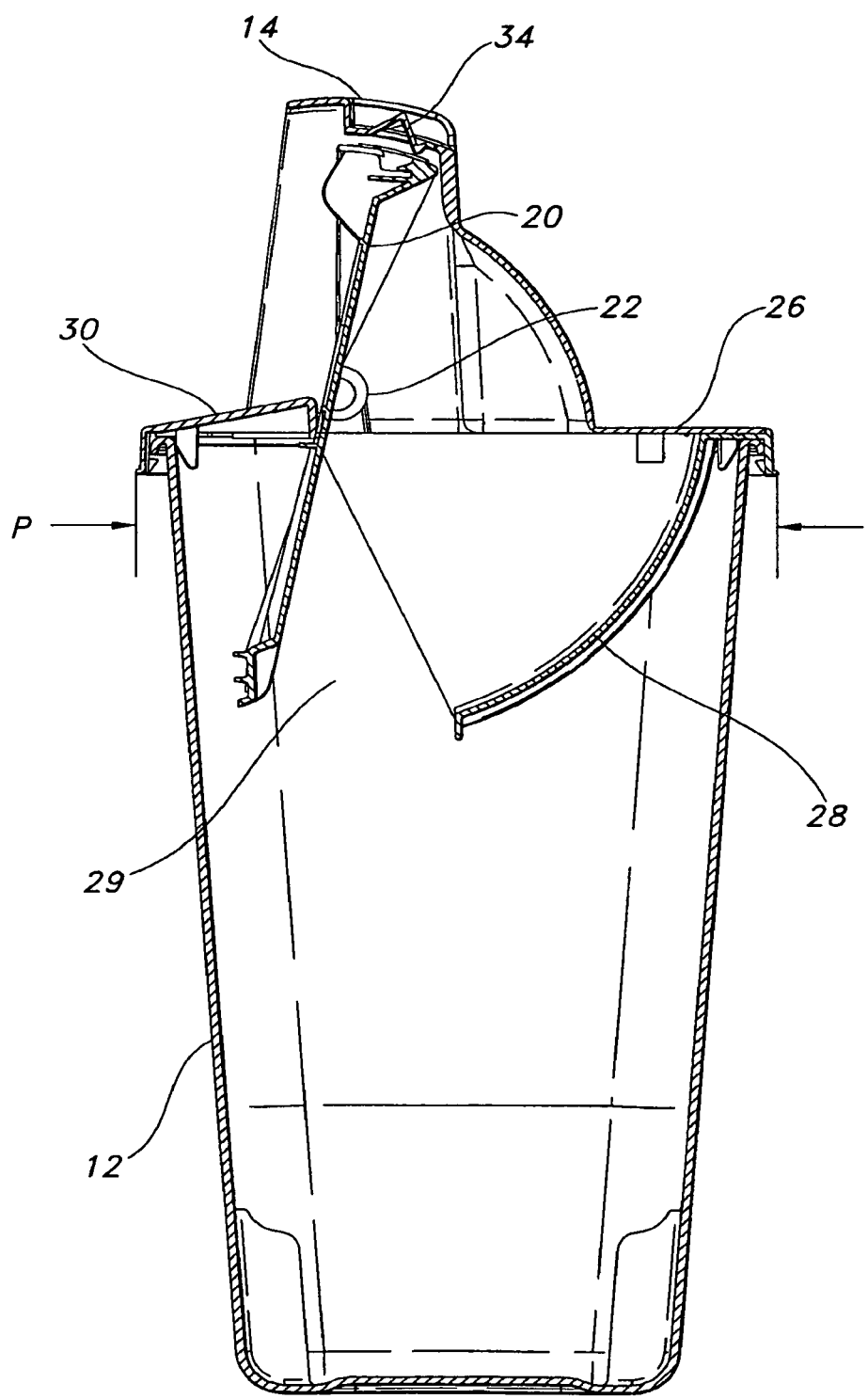
FIG. 3 is a right side cross-sectional view of the assembly illustrated in FIG. 1, with the closure in its closed position.

In operation, and referring again to FIGS. 1 and 3, a counter-balanced door 20 is initially biased to an open position. When a soiled sharp is placed on the door 20 that includes siloxane processing aids, the sharp is more apt to slide or roll down the support surface 24, by virtue of the reduced coefficient of friction of the door surface. The door 20 rotates backwards about its pivot axis 22 toward the closed position under the weight of the sharp, as shown in FIG. 3. The sharp slides off of the treated surface of the door 20 and descends into the medical waste receptacle 12.

In addition to the counter-balanced door 20 made from polyolefin parts modified using siloxane processing aids, the contoured portion 28 (commonly referred to as a cowl) of the lid 26 may also comprise polyolefin parts modified with siloxane processing aids, considering that the medical waste may also contact the exterior surface of the contoured portion before it descends into the receptacle 12. Moreover, any component of the medical waste disposal system may include siloxane processing aids.

In one exemplary embodiment, a moldable thermoplastic resin includes at least polypropylene and at least one siloxane processing aid. In this embodiment, the siloxane processing aid is optionally MB50-321 masterbatch siloxane polymer manufactured by Dow Corning® of Midland, Mich., USA. MB50-321 masterbatch siloxane polymer is a pelletized formulation containing 50% of a functionalized ultra-high molecular weight siloxane polymer. The aggregate polypropylene resin comprises 2 to 10% by weight of MB50-321 masterbatch siloxane polymer. It should be understood that the aforementioned materials are not limited to a particular type of polymer, such as polypropylene or siloxane polymer, as many other polymers and internal release agents are envisioned for use with this invention.

Testing of a counter-balanced door treated with a siloxane additive revealed that the siloxane-treated door had a lower coefficient of friction angle, or friction angle, of approximately 12.5 degrees, as compared with a counter-balanced door not treated with a siloxane additive. In other words, by virtue of the siloxane additive, medical waste slid along the surface of the siloxane-treated door that was oriented at an angle 12.5 degrees less than a door that was not treated with a siloxane additive.

Alternatively, by grafting high weight average molecular weight ($M_w$>100,000) methacrylate polymer onto a polyolefin improves the tensile strength and sag resistance without increasing melt viscosity. The resulting molded polyolefin exhibits decreased surface energy, decreased warping and/or fatigue after processing and improved abrasion resistance. The grafted polyolefin is blended with a polyolefin, providing a modified polyolefin part useful in accordance with the invention.

Figure 2:
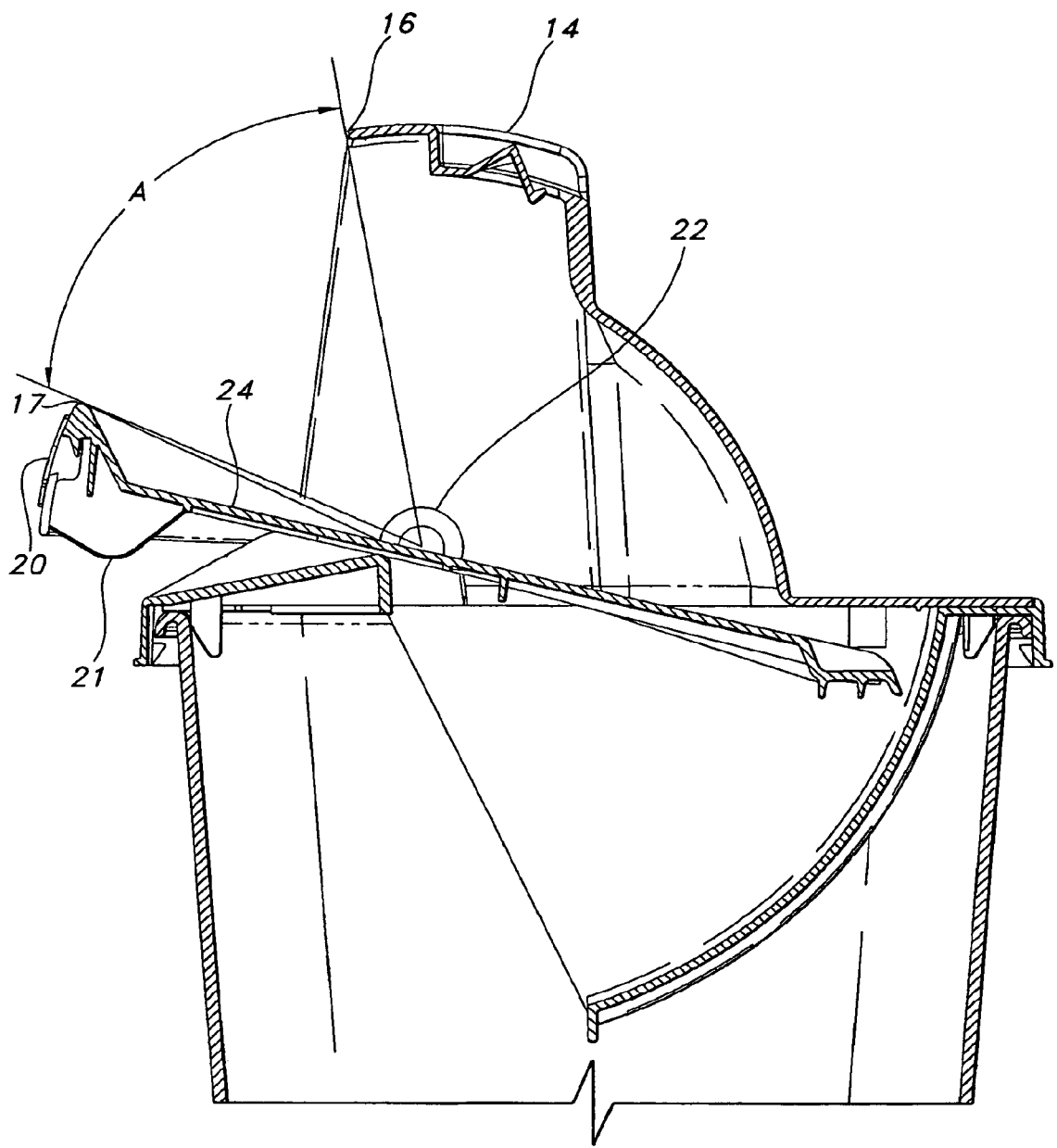
FIG. 2 is a detailed cross-sectional view of the assembly illustrated in FIG. 1.

In addition to incorporating a siloxane processing aid into the moldable thermoplastic resin, a nucleating agent may also be added to the moldable thermoplastic resin to promote dimensional stability and further reduce warping and/or fatigue of the molded article. As discussed in the Background section, an unmodified conventional molded part may exhibit warpage and/or exhibit poor dimensional stability due to anisotropic shrinkage behavior of polypropylene. If a counterbalanced door, such as the door 20 illustrated in FIGS. 1-3, is dimensionally unstable or significantly warped the door may not rotate properly. A dimensional instability shifts the center of gravity of the door, thereby inhibiting or disturbing the auto-rotation feature. Moreover, a dimensional instability may undesirably cause the door to inadvertently contact another surface of the disposal system, yet again inhibiting or disturbing the auto-rotation feature of the door. The addition of a nucleating agent promotes dimensional stability and reduces warpage of the molded article.

A nucleating agent is a chemical substance that forms nuclei for the growth of crystals in a polymer melt. By virtue of the nucleating agent, a higher degree of crystallinity and more uniform crystalline structure is obtained. A thermoplastic polyolefin resin, such as polypropylene, is a semi-crystalline polymer. Nucleating agents increase the crystallization rate and the overall percent crystallinity of the polymer. The faster crystallization rate allows for higher productivity in molding and extrusion processes. The overall percent crystallinity of the polymer improves the stiffness and heat deflection temperature.

By influencing the crystallization process, nucleating agents also affect the differential shrinkage of the base polymer. The selection of a nucleating agent can have a pronounced effect on the dimensional stability of a final part because differential shrinkage is an important factor in part warpage.

A new class of nucleating agents, commonly called "Hyper Nucleating Agents" are now commercially available. Hyper nucleating agents allow for the fastest processing in molding and extrusion processes, while providing the same physical property improvements as traditional nucleating agents. In addition, this new class of nucleating agent promotes greater isotropic shrinkage, which reduces the potential for part warpage.

In another exemplary embodiment, the moldable thermoplastic resin is optionally composed of at least polypropylene and a hyper nucleating agent. In this embodiment, the hyper nucleating agent is optionally Hyperform™ Concentrate HI5-5 nucleating agent manufactured by Milliken chemical of Spartanburg, S.C., USA. Hyperform™ Concentrate HI5-5 nucleating agent is a 5% concentrate of Hyperform™ HPN-68 nucleating agent in a carrier blend composed of a 20 MFR (melt flow rate) polypropylene medium impact copolymer and dispersant. The aggregate polymeric resin comprises about 1.5 to about 2.5% by weight of Hyperform™ Concentrate nucleating agent. It should be understood that the aforementioned materials are not limited to a particular type of polymer, such as polypropylene or Hyperform™ Concentrate HI5-5 nucleating agent, as many other polymers and nucleating agents are envisioned for use with this invention. It should be understood that the nucleating agent is not limited to a "hyper" nucleating agent, or any specific class of nucleating agents.

According to another exemplary embodiment, a door of a medical waste disposal system incorporates both a nucleating agent and a siloxane processing aid. According to this embodiment, the pivoting door would possess the advantages of high dimensional stability, minimal warpage and high lubricity at its outer surfaces.

While preferred embodiments of the invention have been described herein, it will be understood that such embodiments are provided by way of example only. Numerous variations, changes and substitutions will occur to those skilled in the art without departing from the spirit of the invention. For example, the invention may apply to any motive or stationary molded component of a medical waste disposal system. Furthermore, this invention may be applicable to any molded article, upon the surface of which an object slides, translates, or rolls, such as a playground slide, for example. Lastly, in the molding process, the siloxane processing aid and/or nucleating agent is added to a base resin. The base resin may be a polyolefin, such as polypropylene, polyethylene or polyvinyl chloride (commonly known as PVC) or any other polyolefin. Although it should be understood that the base resin is not limited to polyolefin or any other material. Accordingly, it is intended that the appended claims cover all such variations as fall within the spirit and scope of the invention.

What is claimed:

1. A closure for a medical waste receptacle providing a passage through which medical waste is deposited, said closure comprising:
   a door forming at least a portion of said passage, said door being formed from a molded thermoplastic material further comprising a polyolefin resin, a siloxane processing aid, and a nucleating agent, wherein said siloxane processing aid comprises 2 to 10 percent of the total weight of said door.

2. The closure of claim 1 wherein said siloxane processing aid is a siloxane polymer.

3. The closure of claim 2 wherein said siloxane polymer is an ultra-high molecular weight functionalized siloxane polymer dispersed in polypropylene.

4. The closure of claim 1 wherein an external surface of said door manufactured from said polyolefin resin modified with said siloxane processing aid has a reduced coefficient of friction.

5. The closure of claim 1 wherein said nucleating agent comprises about 1.5 to about 2.5 percent of the total weight of said door.

6. The closure of claim 1 wherein said nucleating agent is a hyper nucleating agent.

7. The closure of claim 6 wherein said hyper nucleating agent improves dimensional stability and reduces warpage of said door.

8. The closure of claim 1 wherein said polyolefin resin of said door is selected from the group consisting of polypropylene, polyethylene, polyethylene terpthalate and polyvinyl chloride.

9. The closure of claim 1 wherein said door is pivotably mounted to said closure.

10. A closure for a medical waste receptacle providing a passage through which medical waste is deposited, said closure comprising:
    a door forming at least a portion of said passage, said door being formed from a molded material comprising a polyolefin resin, a siloxane processing aid and a nucleating agent, wherein said nucleating agent comprises about 1.5 to about 2.5 percent of the total weight of said door.

11. The closure of claim 10 wherein said nucleating agent is a hyper nucleating agent.

12. The closure of claim 10 wherein said nucleating agent improves dimensional stability and reduced warpage of said door.

13. The closure of claim 10 wherein said polyolefin resin of said door is selected from the group consisting of polypropylene, polyethylene, polyethylene terpthalate and polyvinyl chloride.

14. The closure of claim 10 wherein said siloxane processing aid comprises 2 to 10 percent of the total weight of said door.

* * * * *

UNITED STATES PATENT AND TRADEMARK OFFICE
CERTIFICATE OF CORRECTION

| | | |
|---|---|---|
| PATENT NO. | : 8,584,885 B2 | Page 1 of 1 |
| APPLICATION NO. | : 12/304352 | |
| DATED | : November 19, 2013 | |
| INVENTOR(S) | : Finnestad et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1122 days.

Signed and Sealed this
Nineteenth Day of April, 2016

Michelle K. Lee
*Director of the United States Patent and Trademark Office*